(12) United States Patent
Rajebi (10) Patent No.: US 11,730,487 B2
(45) Date of Patent: Aug. 22, 2023

(54) VASCULAR HEMOSTASIS SYSTEM

(71) Applicant: Mohammad Reza Rajebi, Dallas, TX (US)

(72) Inventor: Mohammad Reza Rajebi, Dallas, TX (US)

(*) Notice: Subject to any disclaimer, the term of this patent is extended or adjusted under 35 U.S.C. 154(b) by 537 days.

(21) Appl. No.: 17/004,829

(22) Filed: Aug. 27, 2020

(65) Prior Publication Data
US 2021/0059688 A1    Mar. 4, 2021

Related U.S. Application Data

(60) Provisional application No. 62/893,273, filed on Aug. 29, 2019.

(51) Int. Cl.
*A61B 17/132* (2006.01)
*A61B 5/022* (2006.01)

(52) U.S. Cl.
CPC .......... *A61B 17/1322* (2013.01); *A61B 5/022* (2013.01); *A61B 2560/0266* (2013.01)

(58) Field of Classification Search
CPC .............. A61B 17/132; A61B 17/1322; A61B 17/1327; A61B 5/022; A61B 2560/0266; A61B 2017/12004
See application file for complete search history.

(56) References Cited

U.S. PATENT DOCUMENTS

| | | | | |
|---|---|---|---|---|
| 37,156 | A * | 12/1862 | Dunton | A61B 17/1327 606/203 |
| 3,884,240 | A * | 5/1975 | Gilman | A61B 17/132 2/209 |
| 4,233,980 | A * | 11/1980 | McRae | A61B 17/132 601/41 |
| 4,509,528 | A * | 4/1985 | Sahota | A61B 5/6843 600/504 |
| 5,569,297 | A * | 10/1996 | Makower | A61B 17/1325 606/201 |
| 5,728,120 | A * | 3/1998 | Shani | A61B 17/1325 606/120 |
| 5,741,283 | A * | 4/1998 | Fahy | A61B 17/12009 606/151 |

(Continued)

*Primary Examiner* — Ryan J. Severson (57) ABSTRACT

A vascular hemostasis system includes a first compression member and a second compression member separated from the first compression member to create a body part receiving space that is adapted to receive a body part having a vascular opening in need of hemostasis. A compression mechanism connects the first compression member to the second compression member, and the compression mechanism is configured to selectively move the first compression member towards or away from the second compression member to adjust the size of the space and thereby provide varying amounts of compression to the body part. An optional control system includes a detecting system, such as a pulse sensor, and a controller. The controller may be adapted to control the compression mechanism in response to the detecting system. In one version, the compression mechanism includes a locking mechanism that can selectively prevent the first compression member from moving away from the second compression member. The vascular hemostasis system may be used in process to provide hemostasis.

20 Claims, 8 Drawing Sheets

(56) References Cited

U.S. PATENT DOCUMENTS

| | | | | |
|---|---|---|---|---|
| 5,997,564 A * | 12/1999 | Shehata | A61B 17/132 | 606/203 |
| 8,277,483 B2 * | 10/2012 | Teeslink | A61B 17/0057 | 606/213 |
| 8,777,982 B2 * | 7/2014 | Clark | A61B 17/0057 | 602/53 |
| 9,107,671 B2 * | 8/2015 | Guillot | A61B 17/1325 | |
| 9,168,061 B1 * | 10/2015 | DiBenedetto | A61B 17/2812 | |
| 9,393,026 B2 * | 7/2016 | Cully | A61B 17/1325 | |
| 9,445,839 B2 * | 9/2016 | DiBenedetto | A61B 17/44 | |
| 9,839,432 B2 * | 12/2017 | Dahlberg | A61B 17/1325 | |
| 10,463,378 B2 * | 11/2019 | Dou | A61B 17/1325 | |
| 10,588,638 B2 * | 3/2020 | Morrison | A61B 17/135 | |
| 10,653,430 B2 * | 5/2020 | Brown | A61B 5/681 | |
| 11,116,516 B2 * | 9/2021 | Castelli | A61B 17/135 | |
| 11,123,083 B2 * | 9/2021 | Spickermann | A61M 1/3655 | |
| 11,241,160 B2 * | 2/2022 | Shinzato | A61B 5/02007 | |
| 11,389,072 B2 * | 7/2022 | Osoegawa | A61B 5/02422 | |
| 11,432,824 B2 * | 9/2022 | Morrison | A61B 17/135 | |
| 11,510,616 B2 * | 11/2022 | Kopperschmidt | A61B 34/30 | |
| 11,564,694 B2 * | 1/2023 | Bateman | A61B 34/25 | |
| 11,607,228 B2 * | 3/2023 | DeSantis | A61M 39/02 | |
| 2006/0079792 A1 * | 4/2006 | Finburgh | A61B 5/681 | 600/503 |
| 2006/0095073 A1 * | 5/2006 | Beto | A61B 90/50 | 606/201 |
| 2011/0196417 A1 * | 8/2011 | Clark | A61F 5/32 | 606/201 |
| 2012/0150215 A1 * | 6/2012 | Donald | A61B 17/1325 | 606/203 |
| 2012/0191127 A1 * | 7/2012 | Guillot | A61B 17/1325 | 606/203 |
| 2013/0046191 A1 * | 2/2013 | Lin | A61B 5/02233 | 600/500 |
| 2013/0085524 A1 * | 4/2013 | Dahlberg | A61B 17/135 | 606/202 |
| 2013/0289614 A1 * | 10/2013 | Cully | A61B 17/1322 | 606/203 |
| 2014/0031859 A1 * | 1/2014 | D'Andrea | A61B 17/1322 | 606/203 |
| 2015/0164509 A1 * | 6/2015 | Steinbaugh | A61B 17/12 | 606/201 |
| 2015/0366565 A1 * | 12/2015 | Shaltis | A61B 5/0295 | 606/202 |
| 2016/0166283 A1 * | 6/2016 | DiBenedetto | A61B 17/4241 | 606/119 |
| 2016/0271004 A1 * | 9/2016 | Erdinc | A61B 5/6831 | |
| 2017/0273693 A1 * | 9/2017 | Morrison | A61B 17/135 | |
| 2017/0347893 A1 * | 12/2017 | Osoegawa | A61B 5/02233 | |
| 2018/0070838 A1 * | 3/2018 | Shinzato | A61B 5/4848 | |
| 2018/0250016 A1 * | 9/2018 | Dou | A61B 17/1325 | |
| 2018/0250018 A1 * | 9/2018 | Spickermann | A61B 17/1355 | |
| 2018/0279889 A1 * | 10/2018 | Lee | A61B 5/02444 | |
| 2019/0090886 A1 * | 3/2019 | Brown | A61B 17/1322 | |
| 2019/0167273 A1 * | 6/2019 | Morrison | A61B 17/135 | |
| 2019/0350593 A1 * | 11/2019 | Bateman | A61B 34/25 | |
| 2019/0380645 A1 * | 12/2019 | Kopperschmidt | A61B 5/150748 | |
| 2020/0038036 A1 * | 2/2020 | Castelli | A61B 17/1325 | |
| 2020/0289129 A1 * | 9/2020 | Castelli | A61B 17/1325 | |
| 2020/0352577 A1 * | 11/2020 | DeSantis | A61M 39/02 | |
| 2021/0000476 A1 * | 1/2021 | Nishigaya | A61B 17/1325 | |
| 2021/0059688 A1 * | 3/2021 | Rajebi | A61B 17/1322 | |
| 2021/0236141 A1 * | 8/2021 | Brikman | A61B 17/135 | |
| 2022/0031180 A1 * | 2/2022 | Lee | A61B 5/02444 | |
| 2022/0346717 A1 * | 11/2022 | Nguyen | A61B 5/01 | |

* cited by examiner

VASCULAR HEMOSTASIS SYSTEM

PRIORITY

The present application claims the benefit of domestic priority based on U.S. Provisional Patent Application 62/893,273 filed on Aug. 29, 2019, the entirety of which is incorporated herein by reference.

BACKGROUND

Vascular access procedures are increasingly common methods for providing medical treatment and diagnostics. However, effective and efficient hemostasis following the procedure has proven to pose a constant challenge. Vascular access site complications can result in additional trauma to the site and in extreme cases death.

In a vascular access procedure, a catheter is inserted into a blood vessel to gain access to a patient's blood and/or interior of the vessel. Some common vascular access procedures include intravenous medication treatment, chemotherapy, providing access for repeated drawing of blood samples, hemodialysis, blood transfusions, arterial embolization, arterial and venous recanalization, and the like. When the procedure is completed, the catheter must be removed from the blood vessel, and bleeding results at the access site in the blood vessel. This necessitates the need for the healthcare practitioner to take steps to facilitate hemostasis or the stoppage of the flow of blood from the vascular access wound.

Typically, hemostasis is performed by manual compression by a healthcare practitioner applying pressure to the access site by hand to encourage coagulation of blood. However, manual compression has several drawbacks. For example, the process can be uncomfortable for the patient. Point pressure by the practitioner's finger can be painful. The process also inefficiently occupies the time of the healthcare provider as the healthcare provider often has to spend more than thirty minutes with the patient. Also, the patient cannot be moved until the process is completed. To overcome these disadvantages, various vascular closure devices have been developed. However, vascular closure devices to date have not proven to be ideal because they are expensive. In addition, vascular closure devices have been known to fail and cause infection and narrowing or clotting of the artery.

There is therefore a need for an improved system for promoting hemostasis at a vascular access site. There is further a need for an automated or robotic vascular hemostasis system. There is a further need for a vascular hemostasis system that can be used without the need to occupy a healthcare worker for an extended period of time. There is a further need for a vascular hemostasis system that is more comfortable for the patient. There is a further need for a vascular hemostasis system that is affordable.

SUMMARY

The present invention satisfies these needs. In one aspect of the invention, an improved vascular hemostasis system is provided.

In another aspect of the invention, a vascular hemostasis system is provided that can be used without the need to occupy a healthcare worker for an extended period of time.

In another aspect of the invention, a vascular hemostasis system is provided that is comfortable for the patient.

In another aspect of the invention, a vascular hemostasis system is provided that is affordable.

In another aspect of the invention, a vascular hemostasis system comprises a first compression member, a second compression member, and a compression mechanism adapted to compress the first compression member and the second compression member around a boy part in a manner that causes hemostasis.

In another aspect of the invention, a vascular hemostasis system comprises a first compression member and a second compression member separated from the first compression member to create a body part receiving space that is adapted to receive a body part having a vascular opening in need of hemostasis, a compression mechanism connecting the first compression member to the second compression member, wherein the compression mechanism is configured to selectively move the first compression member towards or away from the second compression member to adjust the size of the space and thereby to provide varying amounts of compression to the body part, and a control system comprising a detecting system and a controller, wherein the detecting system is adapted to detect one or more conditions of the body part and to generate an output signal in relation to the one or more conditions and wherein the controller is adapted to control the compression mechanism in response to the output signal.

In another aspect of the invention, a vascular hemostasis system comprises a first compression member and a second compression member separated from the first compression member to create a body part receiving space that is adapted to receive a body part having a vascular opening in need of hemostasis, a compression mechanism connecting the first compression member to the second compression member, wherein the compression mechanism is configured to selectively move the first compression member towards or away from the second compression member to adjust the size of the space and thereby to provide varying amounts of compression to the body part, and a control system comprising a detecting system and a controller, wherein the detecting system is adapted to detect one or more conditions of the body part and to generate an output signal in relation to the one or more conditions and wherein the controller is adapted to control the compression mechanism in response to the output signal, and wherein the detecting system comprises one or more pulse sensors.

In another aspect of the invention, a vascular hemostasis system comprises a first compression member and a second compression member separated from the first compression member to create a body part receiving space that is adapted to receive a body part having a vascular opening in need of hemostasis, a compression mechanism connecting the first compression member to the second compression member, wherein the compression mechanism is configured to selectively move the first compression member towards or away from the second compression member to adjust the size of the space and thereby to provide varying amounts of compression to the body part, and a control system comprising a detecting system and a controller, wherein the detecting system is adapted to detect one or more conditions of the body part and to generate an output signal in relation to the one or more conditions and wherein the controller is adapted to control the compression mechanism in response to the output signal, and wherein the detecting system comprises one or more pulse sensors and wherein the controller is adapted to control the control the compression mechanism by moving the first compression member towards the second compression member when a pulse is detected to compress the body part in the body part receiving space.

In another aspect of the invention, a vascular hemostasis system comprises a first compression member and a second compression member separated from the first compression member to create a body part receiving space that is adapted to receive a body part having a vascular opening in need of hemostasis, a compression mechanism connecting the first compression member to the second compression member, wherein the compression mechanism is configured to selectively move the first compression member towards or away from the second compression member to adjust the size of the space and thereby to provide varying amounts of compression to the body part, and a control system comprising a detecting system and a controller, wherein the detecting system is adapted to detect one or more conditions of the body part and to generate an output signal in relation to the one or more conditions and wherein the controller is adapted to control the compression mechanism in response to the output signal, and wherein the detecting system comprises one or more pulse sensors and wherein the controller is adapted to control the compression mechanism by: moving the first compression member towards the second compression member while a pulse is detected, stopping the movement when a pulse is no longer detected, and locking the first compression member and the second compression member in place for a predetermined amount of time.

In another aspect of the invention, a vascular hemostasis system comprises a first compression member and a second compression member separated from the first compression member to create a body part receiving space that is adapted to receive a body part having a vascular opening in need of hemostasis, a compression mechanism connecting the first compression member to the second compression member, wherein the compression mechanism is configured to selectively move the first compression member towards or away from the second compression member to adjust the size of the space and thereby to provide varying amounts of compression to the body part, and a control system comprising a detecting system and a controller, wherein the detecting system is adapted to detect one or more conditions of the body part and to generate an output signal in relation to the one or more conditions and wherein the controller is adapted to control the compression mechanism in response to the output signal, and wherein the detecting system comprises one or more pulse sensors and wherein the controller is adapted to control the compression mechanism by: moving the first compression member towards the second compression member while a pulse is detected, stopping the movement when a pulse is no longer detected, locking the first compression member and the second compression member in place for a first predetermined amount of time, after the first predetermined amount of time, moving the first compression member away from the second compression member a predetermined distance, and locking the first compression member and the second compression member in place for a second predetermined amount of time.

In another aspect of the invention, a vascular hemostasis system comprises a first compression member and a second compression member separated from the first compression member to create a body part receiving space that is adapted to receive a body part having a vascular opening in need of hemostasis, a compression mechanism connecting the first compression member to the second compression member, wherein the compression mechanism is configured to selectively move the first compression member towards or away from the second compression member to adjust the size of the space and thereby to provide varying amounts of compression to the body part, and a control system comprising a detecting system and a controller, wherein the detecting system is adapted to detect one or more conditions of the body part and to generate an output signal in relation to the one or more conditions and wherein the controller is adapted to control the compression mechanism in response to the output signal, and wherein the detecting system comprises one or more pulse sensors and wherein the controller is adapted to control the compression mechanism by: moving the first compression member towards the second compression member while a pulse is detected, stopping the movement when a pulse is no longer detected, locking the first compression member and the second compression member in place for a first predetermined amount of time, after the first predetermined amount of time, moving the first compression member away from the second compression member a first predetermined distance, locking the first compression member and the second compression member in place for a second predetermined amount of time, after the second predetermined amount of time, moving the first compression member away from the second compression member a second predetermined distance, and locking the first compression member and the second compression member in place for a third predetermined amount of time.

In another aspect of the invention, a vascular hemostasis system comprises a first compression member and a second compression member separated from the first compression member to create a body part receiving space that is adapted to receive a body part having a vascular opening in need of hemostasis, and a compression mechanism connecting the first compression member to the second compression member, wherein the compression mechanism is configured to selectively move the first compression member towards or away from the second compression member to adjust the size of the space and thereby to provide varying amounts of compression to the body part, wherein the compression mechanism comprises a side member connectable to the first compression member at one end and to the second compression member at another end, the first compression member being selectively moveable relative to the side member so that the distance between the first compression member and the second compression member can be varied, and wherein compression mechanism comprises a locking mechanism that can selectively prevent the first compression member from moving away from the second compression member.

In another aspect of the invention, a method of providing vascular hemostasis comprises placing a body part having a vascular opening in need of hemostasis in a body part receiving space between a first compression member and a second compression member; providing a compression mechanism connecting the first compression member to the second compression member, wherein the compression mechanism is configured to selectively move the first compression member towards or away from the second compression member to adjust the size of the space and thereby to provide varying amounts of compression to the body part; detecting a condition in the body part; and controlling the application of compression to the body part in response to the detected condition.

In another aspect of the invention, a method of providing vascular hemostasis comprises placing a body part having a vascular opening in need of hemostasis in a body part receiving space between a first compression member and a second compression member; providing a compression mechanism connecting the first compression member to the second compression member, wherein the compression mechanism is configured to selectively move the first compression member towards or away from the second compression member to adjust the size of the space and thereby to provide varying amounts of compression to the body part; detecting a pulse in the body part; and controlling the application of compression to the body part in response to the detected pulse.

In another aspect of the invention, a method of providing vascular hemostasis comprises placing a body part having a vascular opening in need of hemostasis in a body part receiving space between a first compression member and a second compression member; providing a compression mechanism connecting the first compression member to the second compression member, wherein the compression mechanism is configured to selectively move the first compression member towards or away from the second compression member to adjust the size of the space and thereby to provide varying amounts of compression to the body part; detecting a pulse in the body part; and controlling the application of compression to the body part in response to the detected pulse, and wherein controlling the application of compression comprises: moving the first compression member towards the second compression member while a pulse is detected, stopping the movement when a pulse is no longer detected, locking the first compression member and the second compression member in place for a first predetermined amount of time, after the first predetermined amount of time, moving the first compression member away from the second compression member a predetermined distance, and locking the first compression member and the second compression member in place for a second predetermined amount of time, wherein the first predetermined amount of time and the second predetermined amount of time can be the same or different.

In another aspect of the invention, a method of providing vascular hemostasis comprises placing a body part having a vascular opening in need of hemostasis in a body part receiving space between a first compression member and a second compression member; providing a compression mechanism connecting the first compression member to the second compression member, wherein the compression mechanism is configured to selectively move the first compression member towards or away from the second compression member to adjust the size of the space and thereby to provide varying amounts of compression to the body part; detecting a pulse in the body part; and controlling the application of compression to the body part in response to the detected pulse, and wherein controlling the application of compression comprises: moving the first compression member towards the second compression member while a pulse is detected, stopping the movement when a pulse is no longer detected, locking the first compression member and the second compression member in place for a first predetermined amount of time.

In another aspect of the invention, a method of providing vascular hemostasis comprises placing a body part having a vascular opening in need of hemostasis in a body part receiving space between a first compression member and a second compression member; providing a compression mechanism connecting the first compression member to the second compression member, wherein the compression mechanism is configured to selectively move the first compression member towards or away from the second compression member to adjust the size of the space and thereby to provide varying amounts of compression to the body part; detecting a pulse in the body part; and controlling the application of compression to the body part in response to the detected pulse, and wherein controlling the application of compression comprises: moving the first compression member towards the second compression member while a pulse is detected, stopping the movement when a pulse is no longer detected, locking the first compression member and the second compression member in place for a first predetermined amount of time, after the first predetermined amount of time, moving the first compression member away from the second compression member a predetermined distance, and locking the first compression member and the second compression member in place for a second predetermined amount of time.

In another aspect of the invention, a method of providing vascular hemostasis comprises placing a body part having a vascular opening in need of hemostasis in a body part receiving space between a first compression member and a second compression member; providing a compression mechanism connecting the first compression member to the second compression member, wherein the compression mechanism is configured to selectively move the first compression member towards or away from the second compression member to adjust the size of the space and thereby to provide varying amounts of compression to the body part; detecting a pulse in the body part; and controlling the application of compression to the body part in response to the detected pulse, and wherein controlling the application of compression comprises: moving the first compression member towards the second compression member while a pulse is detected, stopping the movement when a pulse is no longer detected, locking the first compression member and the second compression member in place for a first predetermined amount of time, after the first predetermined amount of time, moving the first compression member away from the second compression member a predetermined distance, and locking the first compression member and the second compression member in place for a second predetermined amount of time, wherein the first predetermined amount of time and the second predetermined amount of time can be the same or different.

In another aspect of the invention, a method of providing vascular hemostasis comprises placing a body part having a vascular opening in need of hemostasis in a body part receiving space between a first compression member and a second compression member; providing a compression mechanism connecting the first compression member to the second compression member, wherein the compression mechanism is configured to selectively move the first compression member towards or away from the second compression member to adjust the size of the space and thereby to provide varying amounts of compression to the body part; detecting a pulse in the body part; and controlling the application of compression to the body part in response to the detected pulse, and wherein controlling the application of compression comprises: moving the first compression member towards the second compression member while a pulse is detected, stopping the movement when a pulse is no longer detected, locking the first compression member and the second compression member in place for a first predetermined amount of time, after the first predetermined amount of time, moving the first compression member away from the second compression member a predetermined distance, locking the first compression member and the second compression member in place for a second predetermined amount of time, and after the second predetermined amount of time, moving the first compression member away from the second compression member a second predetermined distance, and locking the first compression member and the second compression member in place for a third predetermined amount of time.

DRAWINGS

These features, aspects, and advantages of the present invention will become better understood with regard to the following description, appended claims, and accompanying drawings which illustrate exemplary features of the invention. However, it is to be understood that each of the features can be used in the invention in general, not merely in the context of the particular drawings, and the invention includes any combination of these features, where:

DESCRIPTION

The present invention relates to a vascular hemostasis system. In particular, the invention relates to providing automated and/or robotic vascular hemostasis. Although the invention is illustrated and described in the context of being useful for providing hemostasis following a vascular access procedure, the present invention can be useful in other instances. Accordingly, the present invention is not intended to be limited to the examples and embodiments described herein.

Figure 1:
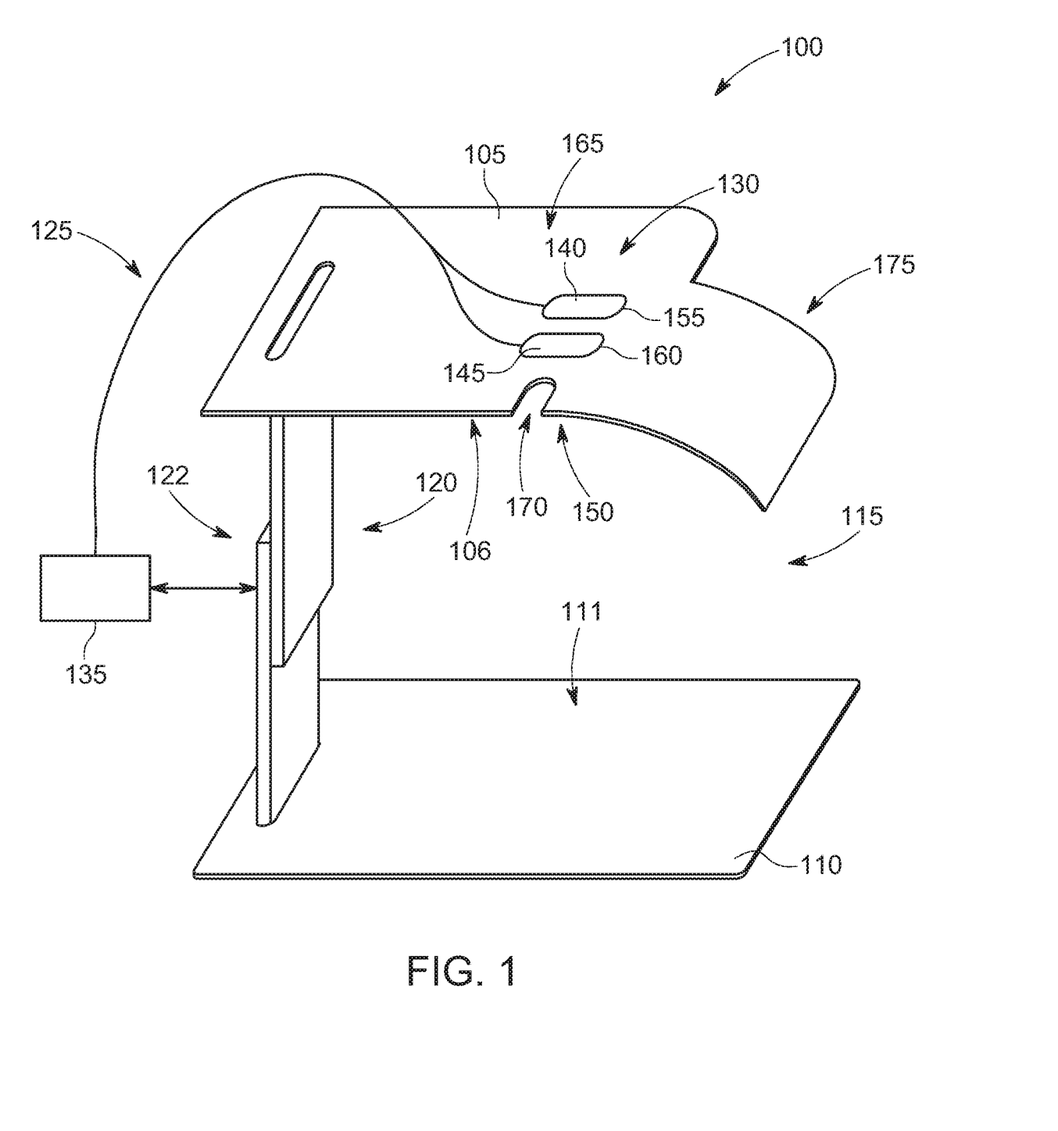
FIG. 1 is a schematic perspective diagram of a vascular hemostasis system according to the invention.

FIG. 1 shows a vascular hemostasis system 100 according to one version of the invention. The vascular hemostasis system 100 includes a first compression member 105 and a second compression member 110. Between the first compression member 105 and the second compression member 110 is a body part receiving space 115 into which a body part can be inserted. The first compression member 105 include an inner surface 106 that is adapted to contact a first side of the body part either directly or indirectly through an intermediary, such as a bandage or gauze. The second compression member 110 includes an inner surface 111 that is adapted to contact a second side of the body part, such as a side opposite to the first side of the body part, either directly or through an intermediary. In one version, the first compression member 105 may be a first plate, and the second compression member 105 may be a second plate. By plate it is meant any solid object that can be flat or curved and that has a surface that can be used to press against a body part. The plate can be planar, partially planar, or non-planar and may have one or more sections that are each planar, partially planar, or non-planar. The first compression member 105 and the second compression member 110 are moveable towards and away from one another to change the size of the space 115. A compression mechanism 120 controls the distance between the first compression member 105 and the second compression member 110 and thus the size or volume of the space 115. The vascular hemostasis system 100 is positionable around a body part where a vascular access site is located. The first compression member 105 is positioned on one side of the body part, such as on top of the body part, and the second compression member 110 is positioned on a second side of the body part, such as under the body part.

The compression mechanism 120 causes the first compression member 105 and the second compression member 110 to move towards one another thereby applying selective compression to the body part and to the vascular access site. This compression helps facilitate and/or promote hemostasis. By vascular access site it is meant any site in the body part into which a catheter has been inserted into a blood vessel to gain access to a patient's blood and/or interior of the vessel and then removed. Some common vascular access procedures include intravenous medication treatment, chemotherapy, providing access for repeated drawing of blood samples, hemodialysis, blood transfusions, arterial embolization, arterial and venous recanalization, and the like. The vascular hemostasis system 100 can also be used to cause hemostasis at any vascular opening into the body part that is in need of closing, such as openings that are created during a medical procedure and those created from trauma. The compression mechanism can include a locking mechanism 122 that locks the first compression member 105 and the second compression member 110 at a particular position relative to one another and/or that prevents the first compression mechanism 105 from moving away from the second compression mechanism 110.

A control system 125 provides automated control over the compression applied by the compression mechanism 120. The control system 125 includes a detecting system 130 and a controller 135. The controller 135 is in communication with the detecting system 130 and controls the compression application process in response to an output signal from the detecting system 130. For example, the detecting system 130 can comprise one or more pulse sensors. In the version of FIG. 1, the detecting system 130 comprises a first pulse sensor 140 and a second pulse sensor 145. The first pulse sensor 140 and second pulse sensor 145 are located on the inner surface 106 of the first compression member 105 at or near a portion 150 of the first compression member 105 that is to be placed in proximity to the body part positioned in the space 115 so that the sensors may be in close proximity to the vasculature of the body part in the space 115. A first sensor visual representation 155 and a second sensor visual representation 160 are provided on the outer surface 165 of the top plate 105 so the position of the first pulse sensor 140 and the second pulse sensor 145 can be visualized.

Additional features may be optionally provided on the vascular hemostasis system 100. For example, in one version, a slot 170 may be provided in the first compression member 105. The slot 170 is a notch in the first compression member 105 that is sized and located to receive a catheter access sheath. The provision of the slot 170 allows the vascular hemostasis system 100 to be installed onto a body part while the catheter access sheath remains within the access site. In another version, the first compression member 105 can include a curved portion 175 that is shaped to contour to the body part that is to be inserted into the space 115. Similarly, though shown as straight, the compression mechanism 120 can have a shape or curvature designed to contour to or around a body part. In another version, an inflatable or non-inflatable cushion may be provided on the inner surface 106 of the first place, on, under, or near the pulse sensor 140 and/or the second pulse sensor 145. The one or more cushions can be used to exert point pressure on the artery to be closed. Optionally, the location of the one or more cushions may be adjustable so the position of the one or more cushions can be adjusted so the one or more cushions exerts point pressure at a desired location on the body part. For example, the one or more cushions may exert point pressure on a nearby vein rather than an artery in case of venous access closure. Any or all of the above parts can be provided alternatively or additionally on the second compression member 110.

Figure 2A:
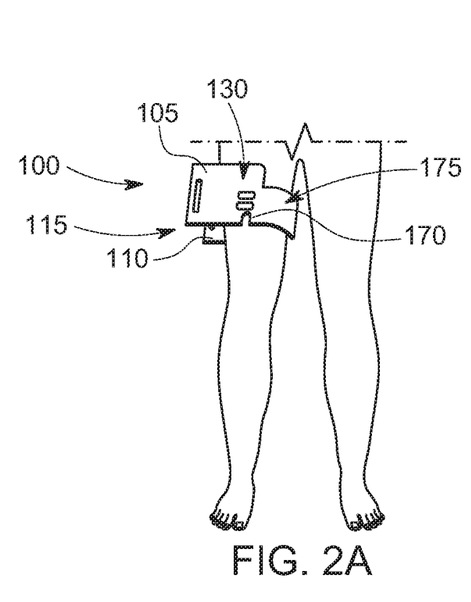
FIG. 2A is a schematic perspective view of the vascular hemostasis system of FIG. 1 in use on a patient's leg.
Figure 2B:
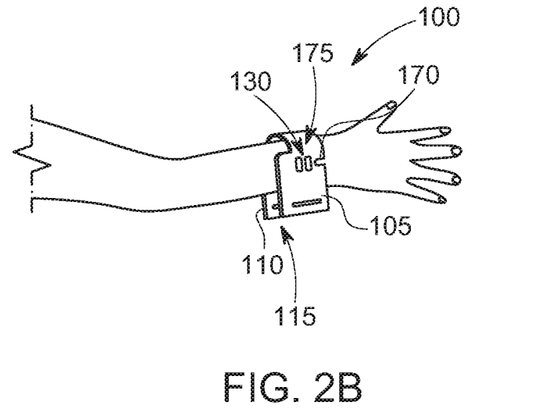
FIG. 2B is a schematic perspective view of the vascular hemostasis system of FIG. 1 in use on a patient's arm.
Figure 2C:
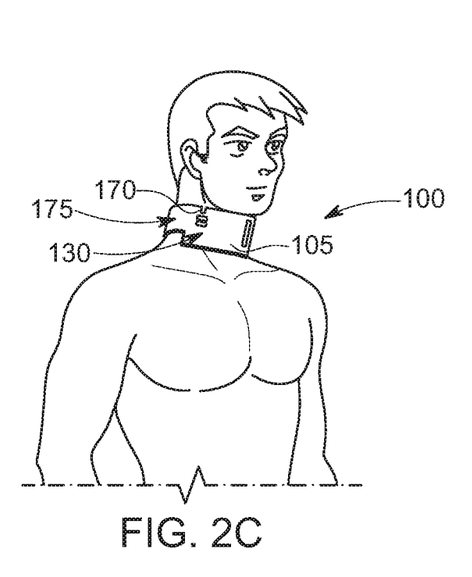
FIG. 2C is a schematic perspective view of the vascular hemostasis system of FIG. 1 in use on a patient's neck.

Following completion of a vascular access procedure, a healthcare practitioner can install the vascular hemostasis system 100 onto the body part where the access site is located. The second compression member 110 may be positioned, for example, below the body part and the first compression member 105 may be positioned, for example, above the body part. Alternatively, the first compression member 105 and second compression member 110 may be positioned on the right side and left side, respectively, of the body part or at any other suitable position on or near the body part. If the catheter sheath remains in the access site, the catheter sheath can be positioned within the slot 170. Examples of the installation of the vascular hemostasis system 100 can be seen in FIGS. 2A through 2C. In FIG. 2A, the vascular hemostasis system 100 is positioned on the leg of a patient at the groin and the femoral artery for patients having undergone a procedure such as a cardiac catheterization, an angiogram, an embolization, a recanalization, or the like. In FIG. 2B, the vascular hemostasis system 100 is positioned on the forearm of a patient at the wrist and the radial artery for patients having undergone a procedure such as a cardiac catheterization, an angiogram, an embolization, a recanalization, or the like. In FIG. 2C, the vascular hemostasis system 100 is positioned on the neck of the patient at the internal jugular vein for patients having undergone procedures such as a right heart cardiac catheterization, a venogram, an IVC filter placement, a recanalization, or the like.

The control system 125, compression mechanism 120, first compression member 105, and second compression member 110 of the vascular hemostasis system 100 cooperate to optimally and automatically perform a compression process that promotes hemostasis of the vascular access site. The compression mechanism 120 includes parts that are slidable relative to one another and a mechanism for causing the parts to selectively slide relative to one another and to selectively prevent sliding. The compression mechanism 120 can comprise any mechanism for causing relative movement between the first compression member 105 and the second compression member 110. For example, the compression mechanism 120 can comprise a gear system, a ratchet system, a telescoping or sliding channel system, or the like. The control system 125 controls the compression mechanism 120 to controllably adjust the distance between the first compression member 105 and the second compression member 110 according to a desired protocol and/or in accordance with the signal from the detecting system 130. The locking mechanism 122 can be part of the control system 125 and/or incorporated into the compression mechanism 120. The locking mechanism can be controlled by the controller 135 to be selectively placed in a locking state whereby the first compression member 105 is locked in position relative to the second compression mechanism 110 or whereby the first compression mechanism 105 is prevented from moving away from the second compression mechanism 110. The locking mechanism can also be placed in an non-locking state whereby the first compression member 105 can move away from or relative to the second compression member 110. The locking mechanism 122 can be provided by a motor or gearing system that locks the movement of the members or can be provided by a physical member that blocks movement of the members, as will be discussed below.

Figure 3:
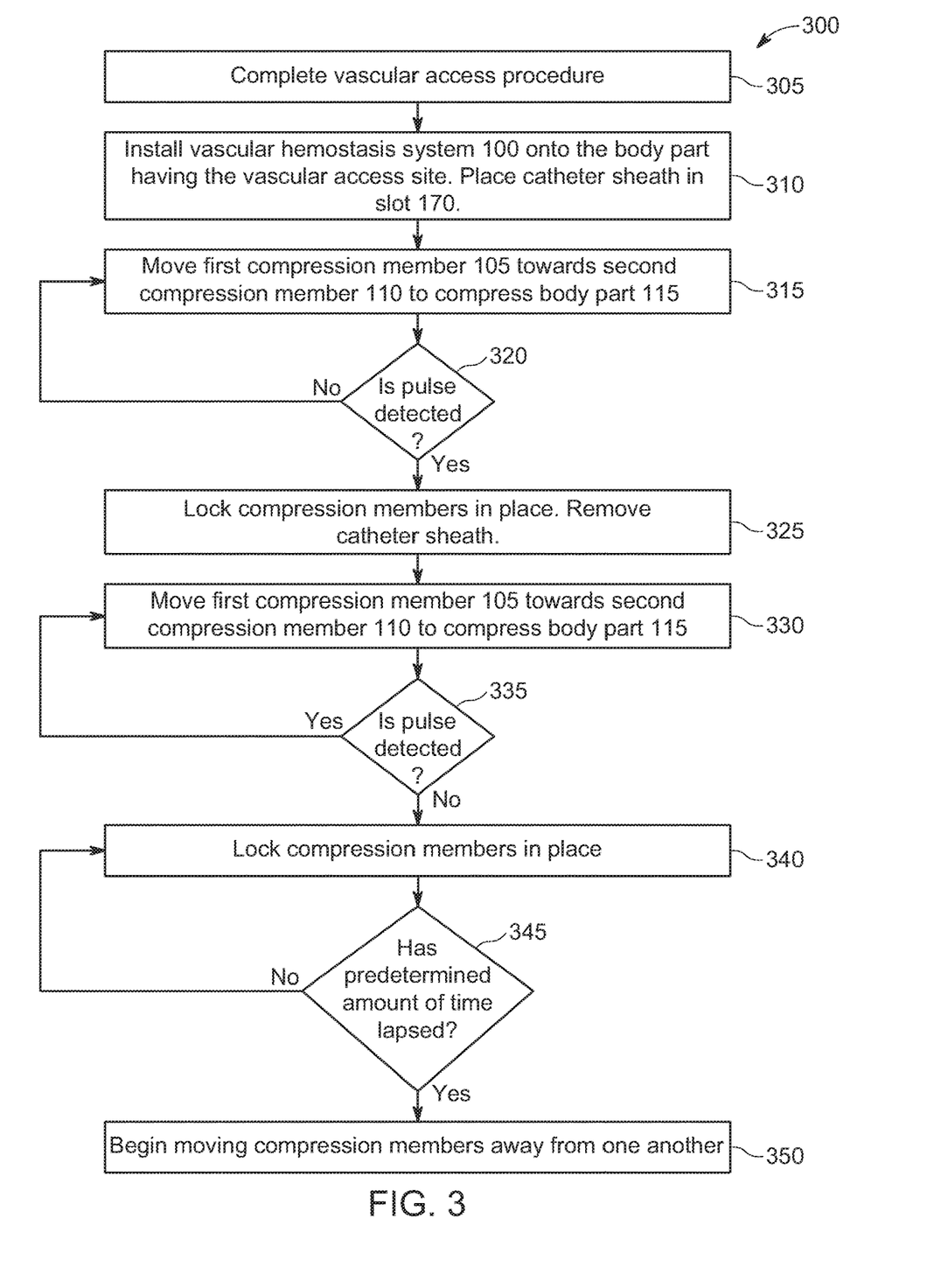
FIG. 3 is a flow chart illustrating a process for promoting vascular hemostasis following a vascular access.

A version of a process 300 for promoting vascular hemostasis following a vascular access procedure is illustrated in FIG. 3. After the vascular access procedure is completed 305, a healthcare practitioner installs 310 the vascular hemostasis system 100 around the body part that contains the vascular access site. If a catheter sheath remains in the access site, it is positioned within the slot 170 in the first compression member 105. The first compression member 105 and the second compression member 110 are then caused to move 315 towards one another each manually or by way of the controller 135 causing the compression mechanism 120 to move the plates. As the first compression member 105 and the second compression member 110 are being moved together, the control system 125 receives a signal from the detecting system 130. In one version, the detecting system 130 comprises one or more pulse sensors 140, 145, and the control 135 monitors the detecting system 130 until a pulse is detected 320. If no pulse is detected, the plates continue to be moved towards the body part and/or compress the body part, and/or the positioning of the system 100 on the body part within the space 115 is adjusted until a pulse is detected. Once a pulse is detected, the movement of the plates is stopped, and the plates are locked in place 325. If the plates are being moved manually, the detection of a pulse by the controller 135 can cause an audible and/or visual signal to activate to indicate to the healthcare practitioner to stop the compression. When the compression is being done automatically, once the controller 135 receives a signal from the detecting system 130 indicative of a pulse, the controller 135 sends a signal to the compression mechanism 120 that causes the compression mechanism 120 to stop the movement of the plates. Optionally, the controller 135 may also produce an audible and/or visual signal a pulse has been detected and the plate movement has been stopped. When the plates are locked in place 325, the catheter sheath is removed. The plates are then caused to move 330 together again, either manually or automatically under the control of the controller 135 and the compression mechanism 120. The pulse is monitored 335, and the plate movement continues until the pulse is no longer detected. The loss of a pulse signal indicates that the compression is sufficient to stop the flow of blood through a blood vessel. At this point, the plates are locked 340 in place. A timer is then initiated within the controller 135, and when a predetermined amount of time has lapsed 345, the controller 130 sends a signal to begin 350 the process of separating 350 the plates from one another and decompressing the body part.

The process 300 of FIG. 3 can be adjusted and/or tailored as desired. For example, rather than a complete lack of pulse at step 320, the controller 135 can instead detect a pulse signal that is reduced by a certain percentage. In one version, a healthcare practitioner can enter into the controller 135 the desired reduction in pulse signal. Similarly, at step 335, instead of the immediate indication of a pulse, a predetermined pulse strength may be utilized instead which may be preprogrammed or enterable by the healthcare practitioner. The amount of time that needs to lapse at step 345 can also be preprogrammed or enterable. The amount of time can be tailored for a particular application. The necessary time can be dependent on various factors including the blood vessel that was accessed, the type of access procedure and thus the size of the wound, the age or other condition of the patient. Also, in addition to or alternatively, the detection system 130 can detect a condition other than pulse, such as the pressure or compressive force being exerted by the plates on the body part.

Figure 4:
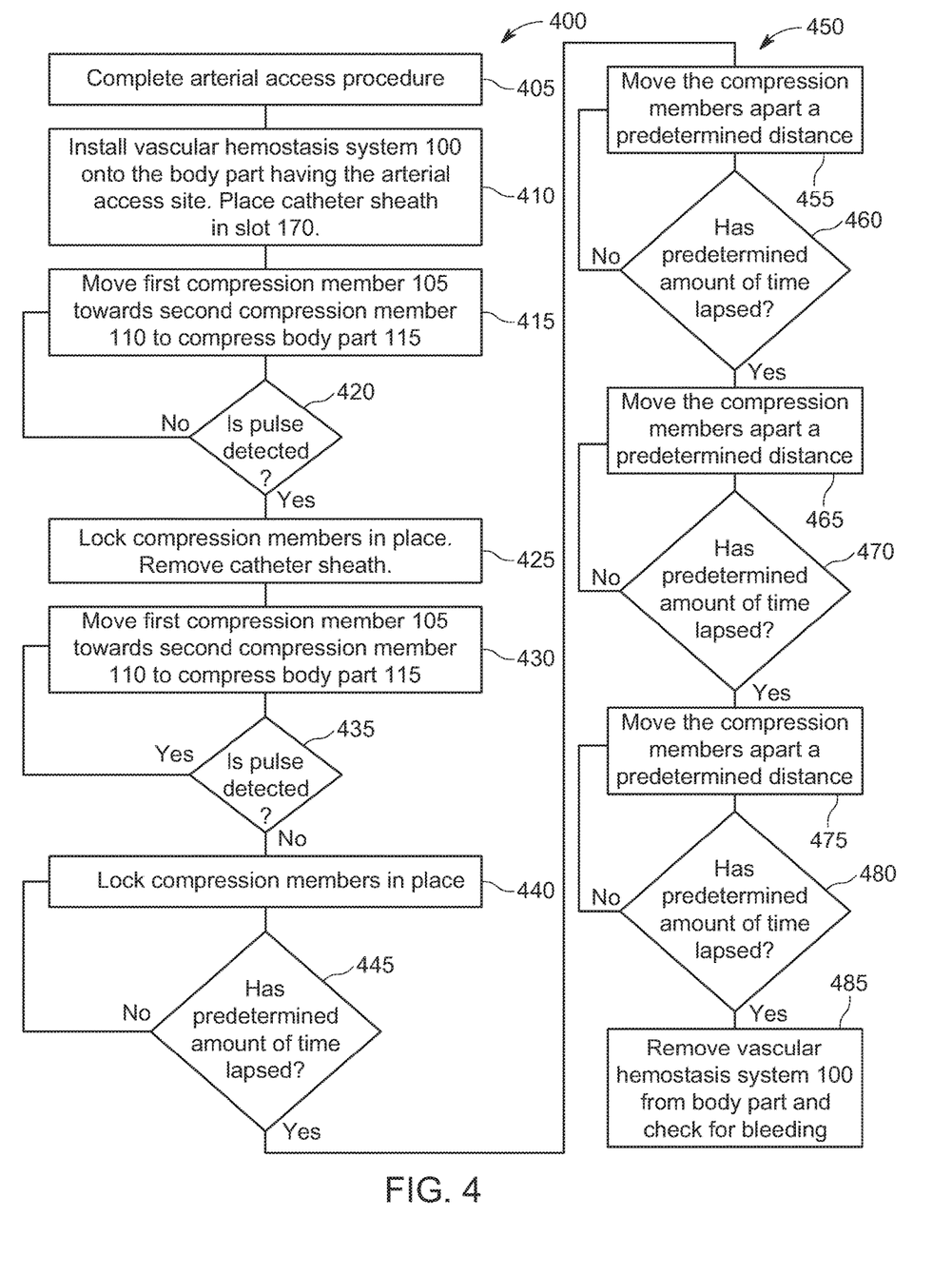
FIG. 4 is a flow chart illustrating a process for promoting vascular hemostasis following an arterial access.

A process 400 particularly useful for promoting vascular hemostasis following an arterial vascular access is illustrated in FIG. 4. After the arterial vascular access procedure is completed 405, a healthcare practitioner installs 410 the vascular hemostasis system 100 around the body part that contains the artery that has been accessed. If a catheter sheath remains in the access site, it is positioned within the slot 170 in the first compression member 105. The first compression member 105 and the second compression member 110 are then caused to move 415 towards one another each manually or by way of the controller 135 causing the compression mechanism 120 to move the plates. As the first compression member 105 and the second compression member 110 are being moved together, the control system 125 receives a signal from the detecting system 130. In one version, the detecting system 130 comprises one or more pulse sensors 140, 145, and the control 135 monitors the detecting system 130 until a pulse is detected 420. If no pulse is detected, the plates continue to be moved towards the body part and/or compress the body part, and/or the positioning of the system 100 on the body part within the space 115 is adjusted until a pulse is detected. Once a pulse is detected, the movement of the plates is stopped, and the plates are locked in place 425. If the plates are being moved manually, the detection of a pulse by the controller 135 can cause an audible and/or visual signal to activate to indicate to the healthcare practitioner to stop the compression. When the compression is being done automatically, once the controller 135 receives a signal from the detecting system 130 indicative of a pulse, the controller 135 sends a signal to the compression mechanism 120 that causes the compression mechanism 120 to stop the movement of the plates. Optionally, the controller 135 may also produce an audible and/or visual signal a pulse has been detected and the plate movement has been stopped. When the plates are locked in place 425, the catheter sheath is removed. The plates are then caused to move 430 together again, either manually or automatically under the control of the controller 135 and the compression mechanism 120. The pulse is monitored 435, and the plate movement continues until the pulse is no longer detected. The loss of a pulse signal indicates that the compression is sufficient to stop the flow of blood through the artery. At this point, the plates are locked 440 in place. A timer is then initiated within the controller 135, and when a predetermined amount of time has lapsed 445, the controller 135 sends a signal to begin the process of separating 450 the plates from one another and decompressing the body part.

The process 450 for separating the plates and decompressing the body part according to the process 400 involves multiple steps of gradually lessening the compression over time. The plates are moved apart 455 a predetermined distance and/or the pressure is reduced by a predetermined amount, and the plates are locked in place. After a second predetermined amount of time has lapsed 460, which can be the same or different than the first predetermined amount of time, the plates are again moved apart 465 a predetermined distance and/or the pressure is reduced by a predetermined amount, and the plates are again locked in place. The process is repeated at steps 470 and 475 until a light compression is maintained for a predetermined period of time 480 after which the vascular hemostasis system 100 can be removed from the body part by a healthcare practitioner, and bleeding at the site can be checked. While the steps of moving the plates apart and locking them in place for a predetermined period of time are shown to occur three times, the process 400 can be altered to have fewer or more repetitions, depending on the situation.

The time periods and plate movements for the process 400 of FIG. 4 can be chosen to best suit a particular situation. The predetermined time periods in steps 445, 460, 470, and 480 can all be same or can vary, and these time periods can be preprogrammed or enterable. Similarly, the distance the plates are moved apart in steps 455, 465, and 475 can be the same or can vary, and these distances can be preprogramed or enterable. In one particular version, the predetermined time periods can range from a 1 minute to about 10 minutes, or from about 2 minutes to about 8 minutes, or from about 4 minutes to about 6 minutes, or about 5 minutes in one particular version. In one version, the distance the plates are moved apart in steps 455, 465, and 475 can range from about 0.5 mm to about 15 mm, or from about 1 mm to about 10 mm, or from about 2 to about 5 mm, or about 2 mm in one particular version. As with the process 300 of FIG. 3, the process of FIG. 4 can be further adjusted and/or tailored as desired.

In one version of the process 400 of FIG. 4, the detecting system 130 comprises a first pulse sensor 140 and a second pulse sensor 145, as shown in FIG. 1. The first compression member 105 of the vascular hemostasis system 100 is positioned so that the first pulse sensor 140 and the second pulse sensor 145 are positioned on the artery to be closed. The second pulse sensor 145 provides a backup to the first pulse sensor 140. If the first pulse sensor 140 fails or is unable to detect a pulse, the signal from the second pulse sensor can be used.

Figure 5:
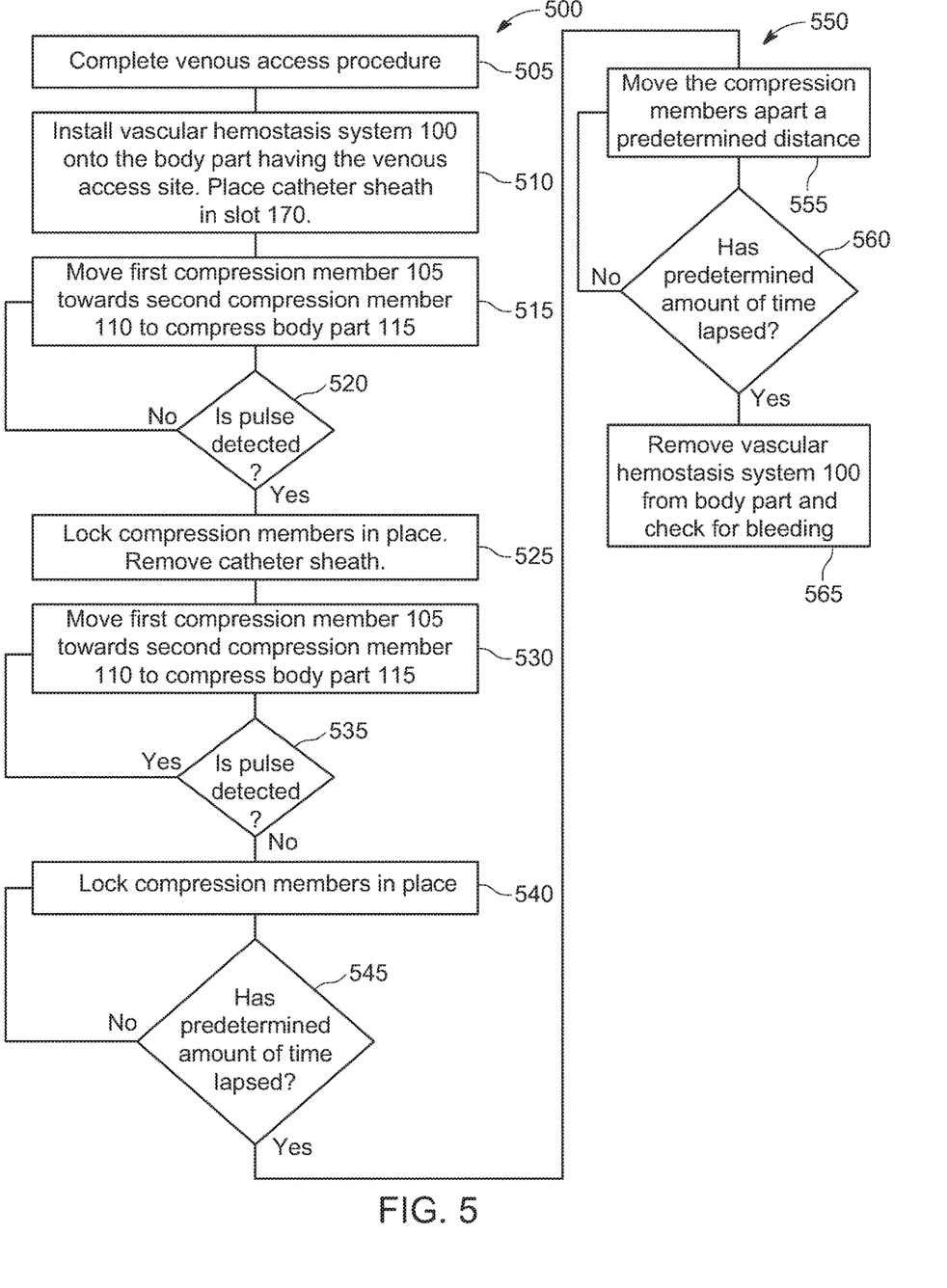
FIG. 5 is a flow chart illustrating a process for promoting vascular hemostasis following a venous access.

A process 500 particularly useful for promoting vascular hemostasis following a venous vascular access is illustrated in FIG. 5. After the venous vascular access procedure is completed 505, a healthcare practitioner installs 510 the vascular hemostasis system 100 around the body part that contains the vein that has been accessed. If a catheter sheath remains in the access site, it is positioned within the slot 170 in the first compression member 105. The first compression member 105 and the second compression member 110 are then caused to move 515 towards one another each manually or by way of the controller 135 causing the compression mechanism 120 to move the plates. As the first compression member 105 and the second compression member 110 are being moved together, the control system 125 receives a signal from the detecting system 130. In one version, the detecting system 130 comprises one or more pulse sensors 140, 145, and the control 135 monitors the detecting system 130 until a pulse is detected 520. The vein does not have a detectable pulse, so instead the detecting system 130 detects a pulse from a nearby artery and is positioned accordingly. If no pulse is initially detected, the plates continue to be moved towards the body part and/or compress the body part, and/or the positioning of the system 100 on the body part within the space 115 is adjusted until a pulse is detected. Once a pulse is detected, the movement of the plates is stopped, and the plates are locked in place 525. Also, the position of the system 100 can then be adjusted to a location over the vein to be closed which is next to the artery. If the plates are being moved manually, the detection of a pulse by the controller 135 can cause an audible and/or visual signal to activate to indicate to the healthcare practitioner to stop the compression. When the compression is being done automatically, once the controller 135 receives a signal from the detecting system 130 indicative of a pulse, the controller 135 sends a signal to the compression mechanism 120 that causes the compression mechanism 120 to stop the movement of the plates. Optionally, the controller 135 may also produce an audible and/or visual signal a pulse has been detected and the plate movement has been stopped. When the plates are locked in place 525, the catheter sheath is removed. The plates are then caused to move 530 together again, either manually or automatically under the control of the controller 135 and the compression mechanism 120. The pulse is monitored 535, and the plate movement continues until the pulse is no longer detected. As discussed above, the detected pulse is the pulse of a nearby artery. The loss of a pulse signal indicates that the compression is sufficient to stop the flow of blood through that artery and such compression is sufficient for compressing the vein with the access site. At this point, the plates are locked 540 in place. A timer is then initiated within the controller 135, and when a predetermined amount of time has lapsed 545, the controller 135 sends a signal to begin the process of separating 550 the plates from one another and decompressing the body part.

The process 550 for separating the plates and decompressing the body part according to the process 500 involves lessening of compression over time. The plates are moved apart 555 a predetermined distance and/or the pressure is reduced by a predetermined amount, and the plates are locked in place. After a second predetermined amount of time has lapsed 560, the vascular hemostasis system 100 can be removed from the body part by a healthcare practitioner, and bleeding at the site can be checked.

The time periods and plate movements for the process 500 of FIG. 5 can be chosen to best suit a particular situation. The predetermined time periods in steps 545 and 560 can be same or can be different, and these time periods can be preprogrammed or enterable. Similarly, the distance the plates are moved apart in step 555 can be preprogramed or enterable. In one particular version, the predetermined time periods can range from a 1 minute to about 10 minutes, or from about 2 minutes to about 8 minutes, or from about 4 minutes to about 6 minutes, or about 5 minutes in one particular version. In one version, the distance the plates are moved apart in steps 555 can range from about 0.5 mm to about 15 mm, or from about 1 mm to about 10 mm, or from about 2 to about 5 mm, or about 2 mm in one particular version. As with the process 300 of FIG. 3 and process 400 of FIG. 4, the process 500 of FIG. 5 can be further adjusted and/or tailored as desired.

In each of the processes discussed, additional steps and/or features can be added. For example, throughout the processes bleeding can be monitored. This can be done by the healthcare practitioner and/or a fluid sensor can be incorporated into the vascular hemostasis system 100 that constantly monitors the presence of excess fluid. In addition, the first compression member 105 and the second compression member 110 may be provided with a rubber coating or the like for patient comfort. Also, the first compression member 105 can be provided with a length adjustment mechanism that allows the length of the first compression member 105 to be adjusted so as to best conform to a body part being compressed.

Figure 6:
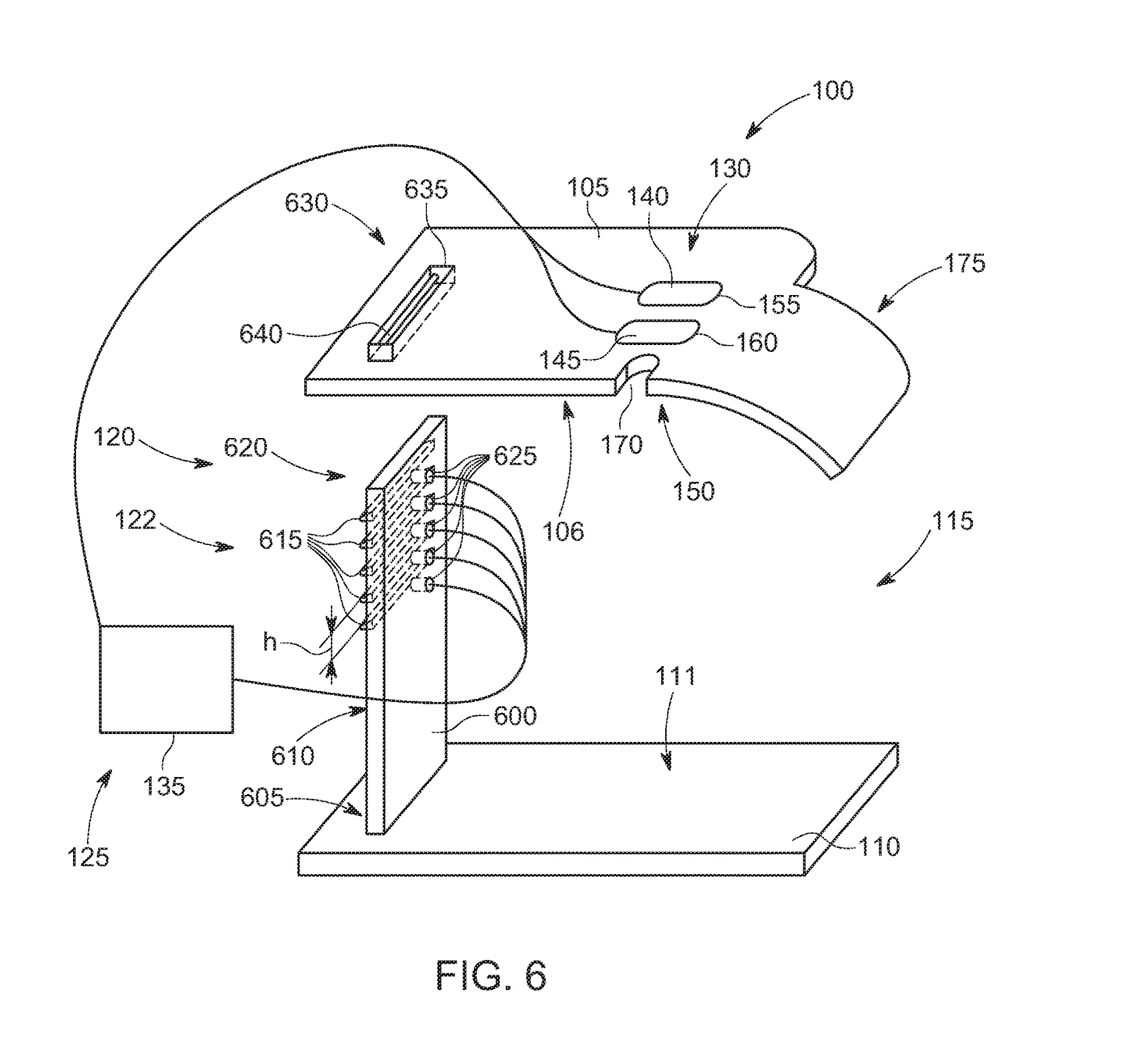
FIG. 6 is a schematic perspective view of a version of a vascular hemostasis system of the invention.

A version of a vascular hemostasis system 100 with a particular compression mechanism 120 is shown in FIG. 6. In this version, the compression mechanism comprises a side member 600, such as a side plate, that is shown assembled onto the second compression member 110. The side member 600 in this version has a bottom end 605 connectable to the second compression member 110. The side member 600 also has a side wall 610 that has one or more projections 615 extending outwardly from the side wall 610 near a top end 620 of the side member 600. In one version, as shown in FIG. 6, a plurality of projections 615 are provided. The projections 615 are longitudinally spaced from one another a predetermined distance, h. The distance, h, between each projection 615 can be the same for each or can be different for one or more of each. As can be seen, associated with each projection 615 is a retraction mechanism 625. Each retraction mechanism 625 is connected to a respective projection 615 and is able to cause the projection 615 to selectively project outwardly from the side wall 610 or to be retracted within the side member 600 so that it does not extend outwardly from the side wall 610. As also shown in FIG. 6, the first compression member 105 includes a side member cooperating mechanism 630. The side member cooperating mechanism 630 in this version includes an opening 635 for slidingly receiving the top end 620 of the side member 600. Within the opening 635 is an engagement member 640 that extends into the opening 635. The engagement member 640 is sized and shaped so that it engages a projection 615 on the side member 600 when the projection 615 is in an extended position but does not engage the projection 615 when the projection 615 is in a retracted position. Thus, when a projection 615 is retracted, the side member 600 can slide through the opening 635 and across the retracted projection 615, but when the projection 615 is extended, the side member 600 is blocked from sliding within the opening 635 by the contact between the extended projection 615 and the engagement member 640. The retraction mechanism 625 for each projection 615 is under the control of the controller 135 so that the controller 135 can control the extension and retraction of each projection 615.

Figure 7A:
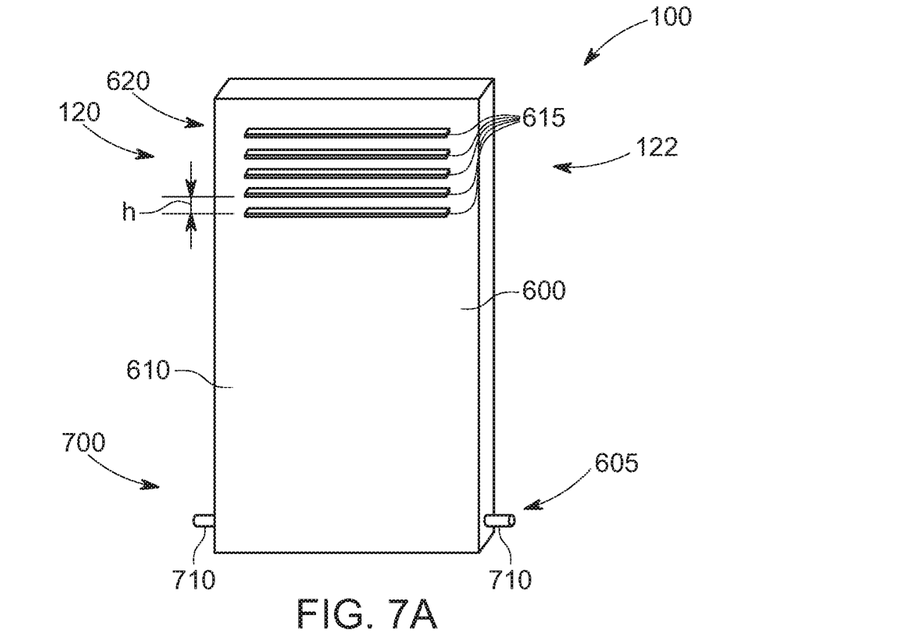
FIG. 7A is a schematic perspective view of a version of a side member of the vascular hemostasis system of the version of FIG. 6.
Figure 7B:
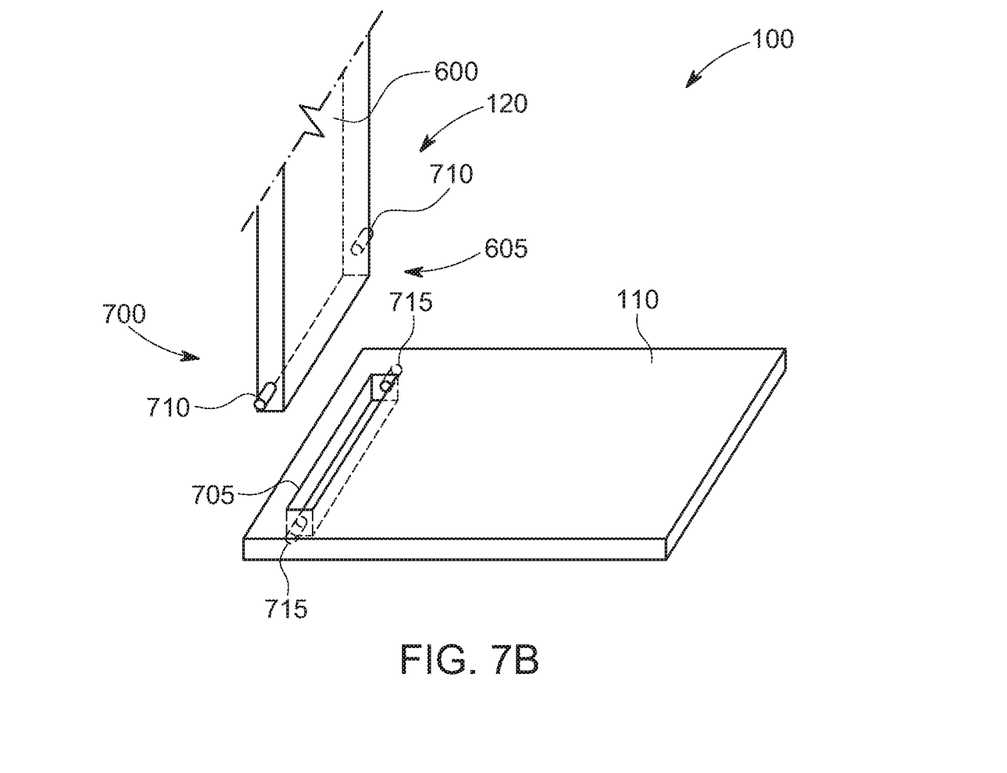
FIG. 7B is a schematic perspective view of a version of a side member and a compression member of the vascular hemostasis system of the version of FIG. 6.

In one version of the version of FIG. 6, as shown in FIGS. 7A and 7B, the side member 600 may be disconnectable from the second compression member 110. FIG. 7A shows a side view of the side member 600 when it is disconnected from the second compression member 110. As can be seen in FIGS. 7A and 7B, a connection mechanism 700 can be provided that allows for selective connection and disconnect of the side member 600 from the second compression member 110. In one version, the second compression member 110 can have a recess 705 that receives the bottom end 605 of the side member 600. The side member 600 can be secured within the recess 705 by any suitable mechanism, such as by one or more posts 710 that are receivable within holes 715 in the recess 705. The posts 710 can be spring loaded and retractable for easy insertion into the holes 715. When connected, the side member 600 and the second compression member 110 form a rigid L-shaped structure. The L-shaped structure can have a 90 degree bend or any can be any angle from about 30 degrees to about 150 degrees. Optionally, the angle can be adjustable. In another version, the side member 600, first compression member 105 and second compression member 110 could also come in a pre-assembled form in a shape defined to more closely contour to the body part, such as a rounded shape or an at least partially semicircular shape.

Figure 8A:
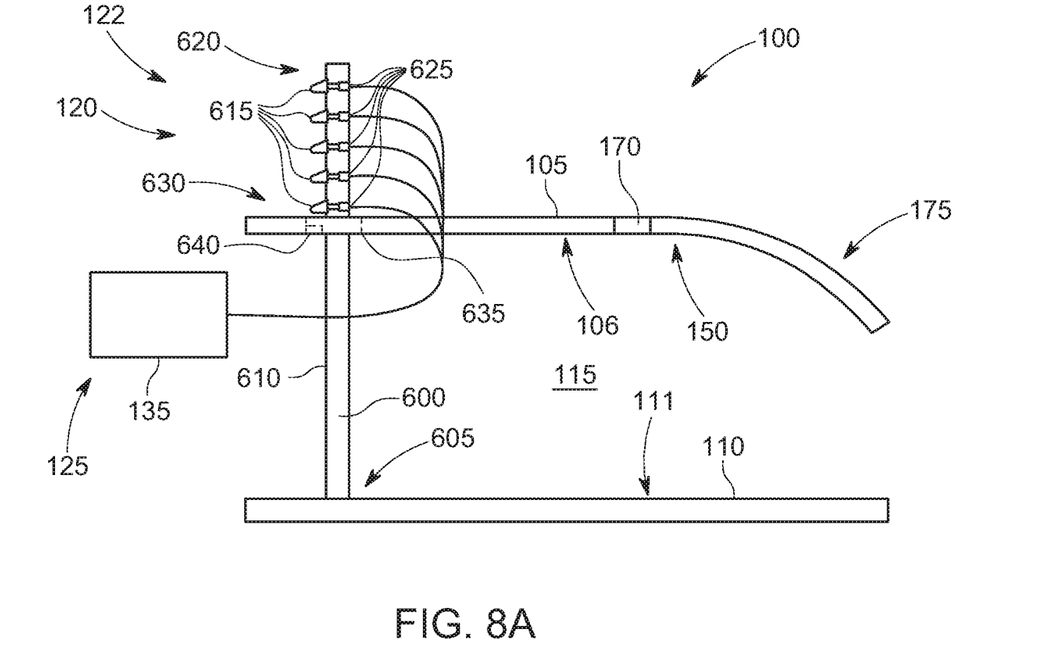
FIG. 8A is a schematic side view of the vascular hemostasis system of FIG. 6 in a first position.
Figure 8B:
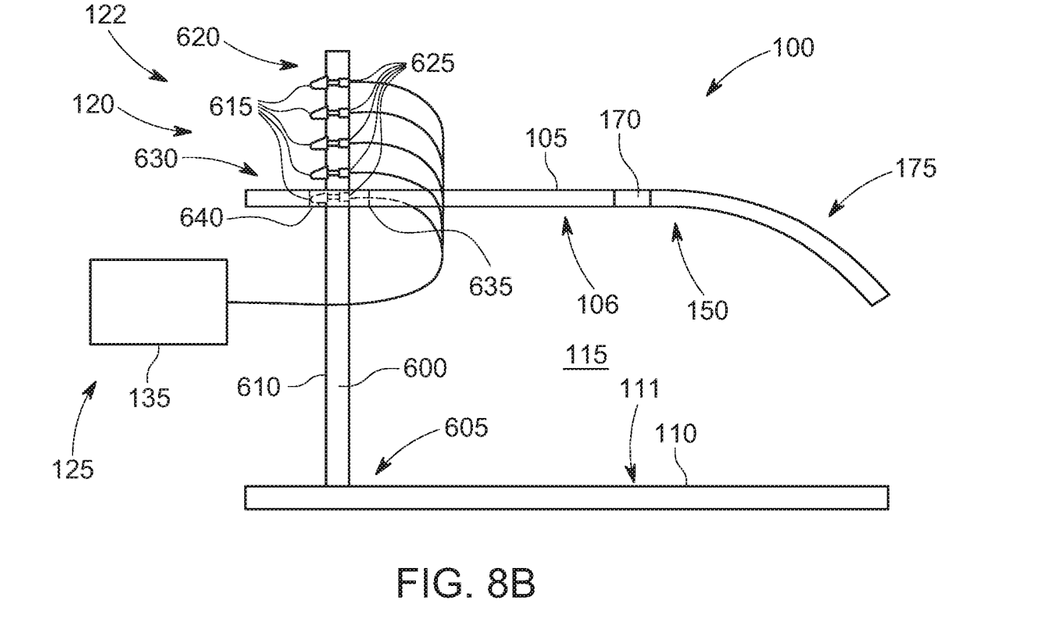
FIG. 8B is a schematic side view of the vascular hemostasis system of FIG. 6 in another position.

FIGS. 8A and 8B show the compression mechanism 120 of the version of FIG. 6 in operation. To install the vascular hemostasis system 100 onto a body part, the controller 135 causes each of the retraction mechanisms 625 to retract their corresponding projection 615 into the side member 600 so that the side member 600 can freely slide through the opening 635 of the first compression member 105. As can be seen in FIGS. 8A and 8B, the retraction mechanism 625 can take the form of an electromechanical piston that moves in and out in response to an electrical signal from the controller 135. When the projections 615 are retracted, the first compression member 105 can be installed onto the top end 620 of the side member 600 and moved towards the second compression member 110 as discussed above to exert compression on a body part located in the space 115. When the first compression member 105 is at a position where a desired compression is applied to the body part, the projections 615 are caused to be extended, as shown in FIG. 8A. The first compression member 105 is then unable to slide upwardly relative to the side member 600 because of the contact between the engagement member 640 and the projection 615. When the time comes to relieve compression of the body part, the controller 135 will cause the projection 615 that is contacting the engagement member 640 to retract, as shown in FIG. 8B. The first compression member 105 is then able to slide upwardly on side member 600 until the next projection 615 is contacted by the engagement member 640. The distance, h, between the projections 615 can be the desired amount of movement between the first compression member 105 and the second compression member 110 during the decompression process or can be a fraction of the amount of movement. When it is a fraction, the controller 135 can retract multiple consecutive projections 615 so that the desired amount of movement is achieved.

The vascular hemostasis system 100 of the present invention offers several advantages heretofore unavailable. For example, the hemostasis system 100 is less expensive than conventional practices and devices. It is automatically controllable and does not require a fulltime healthcare provider to be present for an extended period of time. In addition, the hemostasis device is designed to reduce the risk of vascular injury.

The controller 135 may take the form of any type of computing device known in the art, such as a desktop computer, laptop computer, hand-held computer, printer, or any other type of user device or logic. Further included may also be at least one server coupled to a network, and which is possibly accessible from other devices connected to the network. It should be noted that the server may include any type of computing device/groupware. Each server, if there are more than one, may have connected thereto a plurality of user devices and/or storage. Such user devices may include a desktop computer, laptop computer, hand-held computer, printer, or any other type of user device or logic. It should be noted that a user device may also be directly coupled to the network, in one embodiment.

Methods and systems described herein may be implemented with and/or on virtual systems and/or systems which emulate one or more other systems, such as a UNIX system which emulates a MAC OS environment, a UNIX system which virtually hosts a MICROSOFT WINDOWS environment, a MICROSOFT WINDOWS system which emulates a MAC OS environment, and others known in the art. This virtualization and/or emulation may be enhanced through the use of VMWARE software, in some embodiments.

One or more networks may represent a cluster of systems commonly referred to as a "cloud." In cloud computing, shared resources, such as processing power, connected storage, peripherals, software, data processing, and/or storage, servers, etc., are provided to any device or system in the cloud, preferably in an on-demand relationship, thereby allowing access and distribution of services across many computing systems. Cloud computing typically involves an Internet and/or other high speed data connection (e.g., 4G LTE, fiber optic, etc.) between the systems operating in the cloud, but other techniques of connecting the systems may also be used, such as WiFi, Bluetooth, etc.

In one embodiment, data may be stored to the cloud by one or more medical devices which are configured to communicate with a device in the cloud capable of storing such data. This cloud data storage may be utilized whenever the one or more medical devices are capable of communicating with the device in the cloud and have data to be stored therein. Alternatively or additionally, the one or more medical devices may have local data storage capability, and may utilize the cloud as backup storage and/or overflow storage for data stored locally to the one or more medical devices. In either of these embodiments, when the one or more medical devices communicate with a computing device, the computing device is also provided with access to the data stored to the cloud, either directly by accessing the device storing the data in the cloud, or by receiving the data from the one or more medical devices, which access the data stored to the cloud and send it to the computing device. One of skill in the art would be able to appreciate and understand many other uses of data storage on the cloud, and those uses may be implemented in the embodiments described herein without specifically reciting all such combinations.

An exemplary controller 135 may include a central processing unit, such as a microprocessor, and a number of other units interconnected via a system bus. The controller 135 may include RAM, ROM, an I/O adapter for connecting external devices such as memory to the bus, a user interface adapter for connecting various user interface devices to the bus, such as those internal to the controller 135 (e.g., a touch screen interface, a speaker, a microphone) and devices external to the controller 135 (e.g., a keyboard, a mouse, etc.), a communication adapter for connecting the controller 135 to a network (e.g., a data processing network, communication network, etc.) and a display adapter for connecting the bus to a display screen.

The controller 135 may have resident thereon an operating system, such as the MICROSOFT WINDOWS Operating System (OS), a MAC OS, a UNIX OS, ANDROID, APPLE iOS, or others known in the art. It will be appreciated that embodiments of the present invention may also be implemented on platforms and operating systems other than those mentioned. Embodiments of the present invention may be written using JAVA, XML, C, and/or C++ language, or other programming languages, along with an object oriented programming methodology. Object oriented programming (OOP), which has become increasingly used to develop complex applications, may be used.

In accordance with one embodiment, a user of the controller 135 may install a device application. The device application may be downloaded from an application server accessible to the controller, the application server being of a type known in the art. In another embodiment, the device application may be provided to the controller 135, for example via a computer readable storage medium, such as a CD, MicroSD card, RAM, or ROM, and/or virtually provided via a link and/or pointer that is embedded in a communication received by the controller 135, such as a hypertext link in an email, or HTML pointer in a text message. The controller 135 may then access the device application via the Internet, a WLAN such as a WIFI network, a WAN, a LAN, etc., to install the device application on the controller 135, as would be understood by one of skill in the art upon reading the present descriptions.

The controller 135 may be programmed to control the operation of the vascular hemostasis system 100 by conventional robotics. Robotics is an interdisciplinary branch of engineering and science that includes mechanical engineering, electronic engineering, information engineering, computer science, and others. Robotics deals with the design, construction, operation, and use of robots, as well as computer systems for their control, sensory feedback, and information processing.

These technologies are used to develop machines that can substitute for humans and replicate human actions. Robots can take on any form but some are made to resemble humans in appearance. This is said to help in the acceptance of a robot in certain replicative behaviors usually performed by people.

Although the present invention has been described in considerable detail with regard to certain preferred versions thereof, other versions are possible, and alterations, permutations and equivalents of the version shown will become apparent to those skilled in the art upon a reading of the specification and study of the drawings. For example, the cooperating components may be reversed or provided in additional or fewer number. Also, the various features of the versions herein can be combined in various ways to provide additional versions of the present invention. Furthermore, certain terminology has been used for the purposes of descriptive clarity, and not to limit the present invention. Throughout this specification and any claims appended hereto, unless the context makes it clear otherwise, the term "comprise" and its variations such as "comprises" and "comprising" should be understood to imply the inclusion of a stated element, limitation, or step but not the exclusion of any other elements, limitations, or steps. Therefore, any appended claims should not be limited to the description of the preferred versions contained herein and should include all such alterations, permutations, and equivalents as fall within the true spirit and scope of the present invention.

What is claimed is:

1. A vascular hemostasis system comprising:
   a first compression member and a second compression member separated from the first compression member to create a body part receiving space that is adapted to receive a body part having a vascular opening in need of hemostasis,
   a compression mechanism connecting the first compression member to the second compression member, wherein the compression mechanism is configured to selectively move the first compression member towards or away from the second compression member to adjust the size of the space and thereby to provide varying amounts of compression to the body part, and
   a control system comprising a detecting system and a controller, wherein the detecting system is adapted to detect one or more conditions of the body part and to generate an output signal in relation to the one or more conditions and wherein the controller is adapted to control the compression mechanism in response to the output signal.

2. A vascular hemostasis system according to claim 1 wherein the detecting system comprises one or more pulse sensors.

3. A vascular hemostasis system according to claim 1 wherein the detecting system comprises one or more pulse sensors attached to an inner surface of the first compression member at a position where the one or more pulse sensors can be placed in proximity to the vascular opening in the body part in the space.

4. A vascular hemostasis system according to claim 1 wherein the detecting system comprises one or more pulse sensors and wherein the controller is adapted to control the control the compression mechanism by:
   moving the first compression member towards the second compression member when a pulse is detected to compress the body part in the body part receiving space.

5. A vascular hemostasis system according to claim 1 wherein the detecting system comprises one or more pulse sensors and wherein the controller is adapted to control the compression mechanism by:
   moving the first compression member towards the second compression member while a pulse is detected and
   stopping the movement when a pulse is no longer detected.

6. A vascular hemostasis system according to claim 1 wherein the detecting system comprises one or more pulse sensors and wherein the controller is adapted to control the compression mechanism by:
   moving the first compression member towards the second compression member while a pulse is detected,
   stopping the movement when a pulse is no longer detected, and
   locking the first compression member and the second compression member in place for a predetermined amount of time.

7. A vascular hemostasis system according to claim 1 wherein the detecting system comprises one or more pulse sensors and wherein the controller is adapted to control the compression mechanism by:
   moving the first compression member towards the second compression member while a pulse is detected,
   stopping the movement when a pulse is no longer detected,
   locking the first compression member and the second compression member in place for a predetermined amount of time, and
   after the predetermined amount of time, moving the first compression member away from the second compression member.

8. A vascular hemostasis system according to claim 1 wherein the detecting system comprises one or more pulse sensors and wherein the controller is adapted to control the compression mechanism by:
   moving the first compression member towards the second compression member while a pulse is detected,
   stopping the movement when a pulse is no longer detected,
   locking the first compression member and the second compression member in place for a first predetermined amount of time,
   after the first predetermined amount of time, moving the first compression member away from the second compression member a predetermined distance, and
   locking the first compression member and the second compression member in place for a second predetermined amount of time.

9. A vascular hemostasis system according to claim 8 wherein the first predetermined amount of time is the same as the second predetermined amount of time.

10. A vascular hemostasis system according to claim 8 wherein the first predetermined amount of time is the different than the second predetermined amount of time.

11. A vascular hemostasis system according to claim 1 wherein the detecting system comprises one or more pulse sensors and wherein the controller is adapted to control the compression mechanism by:
    moving the first compression member towards the second compression member while a pulse is detected,
    stopping the movement when a pulse is no longer detected,
    locking the first compression member and the second compression member in place for a first predetermined amount of time,
    after the first predetermined amount of time, moving the first compression member away from the second compression member a first predetermined distance,
    locking the first compression member and the second compression member in place for a second predetermined amount of time,
    after the second predetermined amount of time, moving the first compression member away from the second compression member a second predetermined distance, and
    locking the first compression member and the second compression member in place for a third predetermined amount of time.

12. A vascular hemostasis system according to claim 11 wherein the first predetermined amount of time, the second predetermined amount of time, and the third predetermined amount of time can be the same or different and can be input into the controller and wherein the first predetermined distance and the second predetermined distance can be the same or different and can be input into the controller.

13. A vascular hemostasis system comprising:
    a first compression member and a second compression member separated from the first compression member to create a body part receiving space that is adapted to receive a body part having a vascular opening in need of hemostasis, and
    a compression mechanism connecting the first compression member to the second compression member, wherein the compression mechanism is configured to selectively move the first compression member towards or away from the second compression member to adjust the size of the space and thereby to provide varying amounts of compression to the body part,
    wherein the compression mechanism comprises a side member connectable to the first compression member at one end and to the second compression member at another end, the first compression member being selectively moveable relative to the side member so that the distance between the first compression member and the second compression member can be varied, and wherein compression mechanism comprises a locking mechanism that can selectively prevent the first compression member from moving away from the second compression member.

14. A vascular hemostasis system according to claim 13 wherein the locking mechanism comprises one or more projections on the side member that are each selectively engageable with an engagement member on the first compression member to prevent the first compression member from moving away from the second compression member.

15. A vascular hemostasis system according to claim 13 wherein the locking mechanism comprises a projection on the side member, wherein the projection engages an engagement member on the first compression member to prevent the first compression member from moving away from the second compression member when the projection is in a locking state, and wherein the projection does not engage the engagement member when the projection is not in a locking state.

16. A vascular hemostasis system according to claim 13 wherein the locking mechanism comprises a plurality of longitudinally spaced projections on the side member, wherein each projection can engage an engagement member on the first compression member to prevent the first compression member from moving away from the second compression member when each projection is in a locking state, and wherein each projection does not engage the engagement member when each projection is not in a locking state.

17. A vascular hemostasis system according to claim 13 wherein the locking mechanism can be in a locking state where it prevents the first compression member from moving away from the second compression member and can be in a non-locking state where the first compression member and the second compression member can move away from one another.

18. A vascular hemostasis system according to claim 17 further comprising a controller adapted to place the locking mechanism in the locking state and in the unlocking state in response to a detected condition of the body part.

19. A method of providing vascular hemostasis, the method comprising:
    placing a body part having a vascular opening in need of hemostasis in a body part receiving space between a first compression member and a second compression member;
    providing a compression mechanism connecting the first compression member to the second compression member, wherein the compression mechanism is configured to selectively move the first compression member towards or away from the second compression member to adjust the size of the space and thereby to provide varying amounts of compression to the body part;
    detecting a pulse in the body part; and
    controlling the application of compression to the body part in response to the detected pulse.

20. A method according to claim 19 wherein controlling the application of compression comprises:
    moving the first compression member towards the second compression member while a pulse is detected,
    stopping the movement when a pulse is no longer detected,
    locking the first compression member and the second compression member in place for a first predetermined amount of time,
    after the first predetermined amount of time, moving the first compression member away from the second compression member a predetermined distance, and
    locking the first compression member and the second compression member in place for a second predetermined amount of time,
    wherein the first predetermined amount of time and the second predetermined amount of time can be the same or different.

* * * * *